Figure 1:
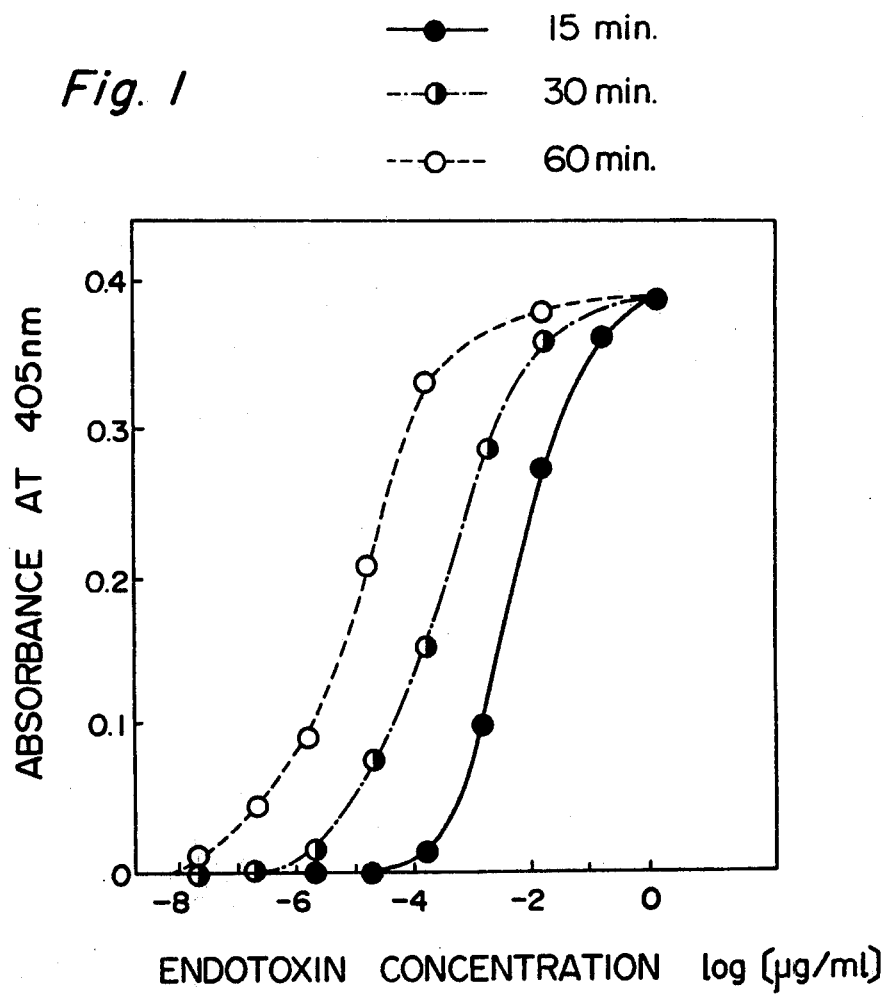

United States Patent [19]

Iwanaga et al.

[11] 4,188,264

[45] Feb. 12, 1980

[54] PROCESS FOR DETERMINING BACTERIAL ENDOTOXIN AND REAGENTS USED THEREFOR

[75] Inventors: Sadaaki Iwanaga, Suita; Takashi Morita, Takatsuki; Shin Nakamura; Kenji Takahashi, both of Inuyama; Makoto Niwa, Sakai, all of Japan

[73] Assignee: Seikagaku Kogyo Co. Ltd., Tokyo, Japan

[21] Appl. No.: 847,582

[22] Filed: Nov. 1, 1977

[30] Foreign Application Priority Data

Jun. 14, 1977 [JP] Japan .................................. 52/70335

[51] Int. Cl.² ............................................ G01N 31/14
[52] U.S. Cl. .................................... 23/230 B; 435/19; 435/23
[58] Field of Search ........................... 195/99, 103.5 R

[56] References Cited

U.S. PATENT DOCUMENTS

| | | | |
|---|---|---|---|
| 3,915,805 | 10/1975 | Levin ............................. | 195/103.5 R |
| 3,944,391 | 3/1976 | Harris et al. ..................... | 195/103.5 R |
| 4,038,029 | 7/1977 | Teller et al. ..................... | 195/103.5 R |
| 4,038,147 | 7/1977 | Reno ............................. | 195/103.5 R |
| 4,104,030 | 8/1978 | Hopkins et al. ................ | 195/103.5 R |
| 4,107,077 | 8/1978 | Sullivan et al. ................ | 195/103.5 R |

OTHER PUBLICATIONS

Nakamura et al, *Biochem. Biophys. Res. Comm.*, 72(3), pp. 902–908, (1976).
Nakamura et al., *J. Biochem.*, 80 pp. 649–652, (1976).
Nakamura et al., *J. Biochem.*, 80, pp. 1011–1021 (1976).
Tai et al., *J. of Biol. Chem.*, 252 (7), pp. 2178–2181, (1977).
Young et al., *J. Clin. Invest.*, 51, pp. 1790–1797, (1972).
Nakamura et al., *J. Biochem.*, 81, pp. 1567–1569 (1977).
Yin et al. *Biochem. Biophys. Acta*, 261, pp. 284–289 (1972).

*Primary Examiner*—Alvin E. Tanenholtz
*Assistant Examiner*—Esther M. Kepplinger
*Attorney, Agent, or Firm*—Sherman & Shalloway

[57] ABSTRACT

A process for determining a bacterial endotoxin, which comprises contacting an assay sample with (A) a material selected from the group consisting of an amoebocyte lysate of horseshoe crab an a pro-clotting enzyme separated from the lysate, and (B) a peptide-type substrate of the formula ($R_1$—Gly—Arg—$R_2$), wherein $R_1$ represents a member selected from the group consisting of an L-amino acid moiety whose N-terminal is protected by a protective group, a peptide moiety consisting of an L-amino acid and protected by a protective group at its N-terminal, a D-amino acid substituted L-amino acid moiety, and a D-amino acid substituted peptide moiety consisting of an L-amino acid, and is bonded to the amino group of the glycine moiety expressed by Gly through a peptide bond; and $R_2$ represents a moiety which is bonded to the C-terminal of an L-arginine moiety expressed by Arg through an acid amide bond and/or ester bond and can be enzymatically hydrolyzed in the presence of the material (A) and the endotoxin to liberate $R_2H$, and/or its mineral acid salt, and detecting the resulting $R_2H$ in which $R_2$ is as defined above; and the above reagent used therefor.

6 Claims, 2 Drawing Figures

PROCESS FOR DETERMINING BACTERIAL ENDOTOXIN AND REAGENTS USED THEREFOR

This invention relates to a process for determining a bacterial endotoxin (frequently abbreviated as "endotoxin" in the present application) utilizing an amoebocyte lysate of horseshoe crab and/or a pro-clotting enzyme separated from the lysate, and to a combination of reagents used therefor. According to the present invention, various advantages such as improved reliability, improved measuring sensitivity, ease of measurement and rapid measurability can be achieved over conventional processes for endotoxin determination utilizing the above lysate or enzyme, and the measuring sensitivity of the conventional processes which is about $10^{-3}$ to $10^{-4}$ μg/ml can be increased to about $10^{-6}$ to $10^{-9}$ μg/ml.

Horseshoe crabs are aquatic animals belonging to the phylum Arthropoda, the class Merostomata, the Subclass Xiphosurida the order Limulidacea, and are scientifically interesting as living fossils. The living species include one genus-one species (*Limulus polyphemus*) along the Atlanta coast of the U.S.A., and two genus-three species near the south east coast of the Asian Continent including Japan, China, Malaysia and Philippines. In Japan, Japanese horseshoe crab (*Tachypleus tridentatus*) inhabits part of the Seto Inland Sea and part of Northern Kyushu.

The circulatory system of horseshoe crab is an open vascular system, and its blood contains amoebocytes. It is known that when a Gram-negative bacterium or an endotoxin is added to a suspension of amoebocytes in a buffer, granules in the amoebocytes soon vanish, and the amoebocytes get out of their shape and fuse, and in the meantime, the cells or endotoxin is surrounded by a fibrous gel. This phenomenon is a body defense reaction of horseshoe crab, and is known as a common nature of horseshoe crabs irrespective of their species. An extract (termed "amoebocyte lysate") obtained by treating the amoebocytes with a hypotonic solution forms a gel by reaction with a tiny amount (about $10^{-3}$ to $10^{-4}$ μg/ml) of endotoxin. Methods for microdetermination of endotoxin utilizing the gelling phenomenon which occurs by the reaction of the amoebocyte lysate of horseshoe crab with a tiny amount of endotoxin have been developed, and already come into use in the fields of medicine, pharmaceutical science and environmental hygienics. It has been widely recognized that there is a fairly high correlation between the measured value of endotoxin utilizing a gelling reaction between the amoebocyte lysate and an endotoxin (especially an endotoxin of a Gram-negative bacterium) and the measured value of a pyrogen test using rabbits for example, if the hyrogen used is an endotoxin. This fact has been utilized, for example, in a preliminary portion of the pyrogen test or in quality control in the manufacture of injectable pharmaceuticals for prevention of a pyrogenic accident caused by the contamination of pharmaceuticals by pyrogen.

Known conventional methods for determination of endotoxins using the amoebocyte lysate of horshore crab include a method in which the hardness of the gel formed as a result of the gelling reaction is evaluated visually by the naked eye, a method wherein the gelling time is measured, a method in which changes in turbidity are traced by using a turbidimeter [described for example, in N. S. Young et al. J. Clin. Invest: 51 1790(1972) and E. T. Yin et al. B.B.A. 261, 284(1972)] and a clotted protein determination method [described for example, in M. Niwa et al. Jpn. J. Med. Sci. Biol. 27, 108–111 (1974)], the first method being most frequently used. Since these prior methods all utilize the gellation phenomenon, they have the defect that the end point of gellation or flocculation is difficult to evaluate. The difficulty is increased when the assay sample has a high viscosity. The measuring sensitivity of endotoxin by these conventional methods is at best about b $10^{31\ 3}$ to $10^{-4}$ μg/ml although it can vary according, for example, to the activity of the amoebocyte lysate, the type of endotoxin, and the means and standards of evaluation, and it has been desired to provide a determination method having higher sensitivity.

These prior techniques are advantageous in sensitivity, rapidity and simplicity over the method of determining endotoxins by a pyrogen test or fatal test using an experimental animal. However, since they rely on the direct or indirect determination of the degree of gellation, they cannot substantially avoid retardation or inhibition of gellation in the presence of a gellation inhibitor in the assay sample or acceleration of gellation in the presence of a certain protease in the assay sample.

The present inventors have worked on the gellation mechanism of the amoebocyte lysate of horseshoe crab, and found that an endotoxin can be detected and determined with superior reliability and very high sensitivity on the basis of a new mechanism which quite differs from the gellation phenomenon utilized in the prior methods.

The investigations of the present inventors led to the discovery that when (A) a material selected from an amoebocyte lysate of horseshoe crab and a pro-clotting enzyme separated from the lysate and (B) a peptide-type substrate of a specified structure are contacted with an assay sample, a specified terminal structure portion of the substrate (B) is freed by enzymatic hydrolysis if the assay sample contains an endotoxin, and that the amount of the freed terminal portion increases with increasing amount of the endotoxin present in the assay sample. They also found that the substance freed by this hydrolysis can be detected and determined, and the measurement sensitivity is so good as to enable a tiny amount (about $10^{-6}$ to about $10^{-9}$ μg/ml) of an endotoxin to be detected and determined.

It was also found that the peptide-type substrate (B) must have a structure in which L-amido acids are connected in the order or arginine (Arg) and glycine (Gly) starting at the C-end of the terminal portion to be cut, and that the peptide-type substrate (B) of this specified structure, in the presence of an endotoxin, acts on the pro-clotting enzyme present in the amoebocyte lysate of horseshoe crab or separated from it, and specifically undergoes enzymatic hydrolysis by the generated active enzyme and thus frees the terminal portion. It was also found that the amount of the terminal portion to be freed shows a good correlation with the amount of the endotoxin within a certain range, and the amount of the terminal portion freed increases proportionally to the increase of the endotoxin content. They also found that since only the pro-clotting enzyme is activated in the presence of endotoxin quantitatively and is involved in the cutting of the terminal portion of the peptide-type substrate (B), the endotoxin can be conveniently detected and determined without any adverse effect of other proteases and/or esterases which may be present in the amoebocyte lysate or the enzyme separated from the lysate or other proteases and/or esterases which may be present in the assay sample.

The detailed mechanism of the activation of the pro-clotting enzyme has not been entirely known, but it is presumed that the pro-clotting enzyme (an amidase precursor and/or an esterase precursor) in the amoebocyte lysate is activated by the action of endotoxin and thus converted to a clotting enzyme (amidase-like substance and/or esterase-like substance), and that the activated enzyme selectively acts on the terminal portion of the peptide-type substrate (B) of the specified structure to cut and free it.

It is an object of this invention therefore to provide a superior process for detecting and/or determining endotoxins utilizing the amoebocyte lysate of horseshoe-crab and/or a pro-clotting enzyme separated from the lysate.

Another object of this invention is to provide a combination of reagents used in this process.

The above and other objects and advantages of the invention will become more apparent from the following description.

According to the present invention, there are provided a process for determining a bacterial endotoxin, which comprises contacting an assay sample with (A) a material selected from the group consisting of an amoebocyte lysate of horseshoe crab and a pro-clotting enzyme separated from the lysate, and (B) a peptide-type substrate of he formula $$R_1-Gly-Arg-R_2 \qquad (1)$$

wherein $R_1$ represents a member selected from the group consisting of an L-amino acid moiety whose N-terminal is protected by a protective group, a peptide moiety consisting of an L-amino acid and protected by a protective group at its N-terminal, a D-amino acid substituted L-amino acid moiety, and a D-amino acid substituted peptide moiety consisting of an L-amino acid, and is bonded to the amino group of the glycine moiety expressed by Gly through a peptide bond; and $R_2$ represents a moiety which is bonded to the C-terminal of an L-arginine moiety exprssed by Arg through an acid amide bond and/or an ester bond and can be enzymatically hydrolyzed in the presence of the material (A) and the endotoxin to liberate $R_2H$, and/or its mineral acid salt, detecting the resulting $R_2H$ in which $R_2$ is as defined above, and if desired, determining it; and a reagent for detecting or determining an endotoxin which comprises a combination of the components (A) an (B).

The amoebocyte lysate of horseshoe crab used in this invention can be obtained by a known procedure which involves treating amoebocytes contained in the blood of horseshoe crab with a hypotonic solution [for example, E. T. Yin et al. B.B.A. 261, 284 (1972), and S. Nakamura et al. J. Biochem., 80, 1011–1021 (1976)]. It is also available commercially under the registered trademarks Pregel (Teikoku Hormone Co., Ltd., Japan), Pyrotest (Difco Rabo., U.S.A.), Pyrogent (Mallinckradt Chem. Works, U.S.A.), Pyrostat (Worthington, U.S.A.), LAL (Haemachem, U.S.A.), and Limulus Amebocyte Lysate (LAL) Microbiological Associates, U.S.A.).

The resulting amoebocyte lysate may be subjected to such a procedure as column chromatography, electrophoresis, isoelectric fractionation (Electro-focusing, a tradename LKB), affinity chromatography, or gel filtration to separate pro-clotting enzyme in the lysate. The separating procedure is described, for example, in N. S. Young et al., J. Clin. Invest. 51, 1790 (1972), J. S. Salivan et al., B.B.R.C. 66, 848 (1975), J. Y. Tai et al., J. Biol. Chem. 252, 2178 (1977), and S. Nakamura et al., J. Biochem. 80, 1011 (1976), and can be used to produce the pro-clotting enzyme used in the present invention.

If the clottable protein contained in the amoebocyte lysate is removed by using a gel filtration procedure, the sensitivity of assay can be increased to at least 10 times.

Examples of the protective group at $R_1$ in the peptide-type substrate (B) expressed by formula (1) are α-N-benzoyl groups, α-N-carbobenzoxy, N-tert.-butoxycarbonyl and p-toluenesulfonyl groups. Specific examples of $R_1$ are Bz-Ile-Glu(-γ-OMe)-, Z-Ile-Glu(-γ-OMe)-, Tos-Ile-Glu-, Z-Ile-Glu-, Bz-Val-, Boc-Val-Leu-, Bz-Val-Leu-, (D-amino acid moiety)-Ile-Glu-(γ-OMe)-, (D-amino acid moiety)-Val-Leu-, Bz-Val-Ser-, (D-amino acid moiety)-Ser-Gly-Val-Ser-Gly-Arg-,Boc-Val-Ser-, Boc-Leu-, Boc-Ser-, Z-Leu-, Z-Ser-, Z-Val-, (D-amino acid moiety)-Val-Leu-, (D-amino acid moiety)-Val-Ser-, (D-amino acid moiety)-Leu-, and (D-amino acid moiety)-Ser-. In the above and other exemplifications in this application, Bz represents a benzoyl group; Z, a carbobenzoxy group; Boc, a tert-butoxycarbonyl group; Tos, a p-toluenesulfonyl group; Me, a methyl group; Ile, L-isoleucine; Glu, L-glutamic acid; Val, L-valine, Ser, L-serine; and Leu, L-leucine.

$R_2$ in the peptide-type substrate (B) of formula (1) is a protective group for the C-terminal of the L-arginine moiety expressed by Arg, and is bonded to the C-terminal by an acid amide bond and/or an ester bond. In the presence of the component (A) and the endotoxin, the acid amide bond and/or ester bond undergoes the action of enzymatic hydrolysis to liberate $R_2H$. According to the method of this invention, the presence or absence (when $R_2H$ is not liberated) of an endotoxin can be known by detecting the liberated $R_2H$. The amount of the endotoxin can be known by determining the amount of the $R_2H$. Hence, $R_2$ may be a moiety capable of permitting the detection and/or determination of the liberated $R_2H$. Any desired species of $R_2$ which can be detected by, for example, a physical or chemical means can be selected for use in this invention. A suitable detecting means is one in which $R_2$ capable of generating chromogenic $R_2H$ is used, and the presence and amount of $R_2H$ is determined by an optical means such as the measurement of its absorbance. Examples of $R_2$ suitable for use in this procedure are a para-nitroanilide group (PNA) which generates a compound $R_2H$ forming a yellowish orange color, a 5-nitro-α-naphthylamide (5-NNA) which generates a compound $R_2H$ forming an orange yellow color, and β-naphthylamide (β-NA), α-naphthyl ester (α-NE), β-naphthyl ester (β-NE), indoxyl ester (INDE), N-methyl indoxyl ester (MINDE), (4-methyl)umbelliferyl ester and resorfin ester which generate fluorescent compounds $R_2H$.

Examples of suitable peptide-type substrates (B) of formula (1) are:

Bz-Ile-Glu(γ-OMe)-Gly-Arg-PNA,
Tos-Ile-Glu-Gly-Arg-PNA,
Boc-Val-Leu-Gly-Arg-PNA,
Bz-Val-Gly-Arg-PNA,
Bz-Val-Ser-Gly-Arg-5-NNA,
Bz-Val-Leu-Gly-Arg-β-NA,
Tos-Ile-Glu-Gly-Arg-β-NE,
Boc-Val-Gly-Arg-INDE,
Z-Val-Leu-Gly-Arg-4-methyl umbelliferyl ester,
Bz-Val-Ser-Gly-Arg-resorufin ester, D-Val-Ser-Gly-Val-Ser-Gly-Arg-MINDE,
Boc-Val-Ser-Gly-Arg-PNA,
Boc-Val-Gly-Arg-PNA,
Boc-Leu-Gly-Arg-PNA,
Boc-Ser(-o-Bz)-Gly-Arg-PNA,
D-Val-L-Leu-Gly-Arg-5NNA,
D-Val-L-Leu-Gly-Arg-α-NA, and
D-Val-L-Leu-Gly-Arg-Resorufin.

Some of these substrates (B) are commercially available, and some can be prepared by a combination of usual peptide synthesizing methods. Basically, they can be prepared, for example, by the following two methods. One method is a stepwise method which comprises coupling a compound of $R_2$ in formula (1) with Arg, and then successively coupling Gly and the other amino acid residues. The other method comprises forming an amino acid arrangement of the desired peptide structure stepwise, and finally coupling a compound $R_2$ with the C-terminal of Arg of the peptide structure.

Examples of available coupling methods are the DCC method developed by J. C. Sheehan et al. [Jacs 77, 1067 (1955) and Jacs., 78, 1367 (1956)] and its improvement, a mixed acid anhydride method which comprises forming an acid anhydride of ethylchlorocarboxyic acid or i-butylchlorocarboxylic acid with an amino acid, and condensing the amine component, and the HOSu-DCC method which comprises reacting an acid component with N-oxysuccinimide to form N-oxysuccinimide ester, and condensing it by adding an amine component and DCC.

The guanidine group of Arg can be protected by a nitro group; the —OH group of Ser, by a benzyl group; and the γ-carboxyl group of glutamic acid, as a methyl ester or a benzyl ester.

The measurement by an optical means as described above is based on the fact that $R_2H$ formed by enzymatic hydrolysis has quite a different absorption spectrum from that of the substrate (B). This measuring method has greatly advanced in recent years as an assay method for enzymes using chromogenic substrates (New Method for the Analysis of Coagulation Using Chromogenic Substrates: Proceedings of the Symposium of the Deutsche Gesellschaft für Klinische Chemie Titisee, Breisgan, West Germany, July 1976, Editor I. Witt Walter de Gruyter-Berlin, New York 1977).

The measurement method is described in more detail by referring to the use of Bz-Ile-Glu(-γ-OMe)-Gly-Arg-PNA.HCl as a substrate.

This substrate has an absorption maximum having a molecular extinction coefficient of 12,000 at 316 nm, and its absorption near 405 nm is not clear and is very little. On the other hand, para-nitroaniline formed and liberated from the substrate by enzymatic hydrolysis has an absorption maximum of a molecular extinction coefficient of 13,200 at 380 nm, and a clear and great absorption having a molecular extinction coefficient of 9620 at 405 nm. Hence, the amount of the para-nitroaniline is measured and determined by the spectrophotometric method at 405 nm, and the amount of the endotoxin proportional to the amount of the para-nitroaniline can be easily determined by using a standard curve (calibration curve) prepared in advance using a standard sample containing a known amount of endotoxin.

The following compounds having fluorescence which are generated by enzymatic hydrolysis can be determined by an ordinary fluorescent spectrophotometer by selecting the excitation wavelength (ex.) and the measurement wavelength em.) as tabulated below.

| Compound $R_2H$ | Structural formula | Excitation wavelength (ex.; nm) | Measurement wavelength (em.; nm) |
| --- | --- | --- | --- |
| β-Naphtylamine | naphthalene-NH₂ | 335 | 410 |
| α-Naphthol | 1-naphthol | 330 | 460–470 |
| β-Naphthol | 2-naphthol | 330 | 410 |
| Indoxyl | 3-hydroxyindole | 395 | 470 |
| N-methylindoxyl | N-methyl-3-hydroxyindole | 430 | 500 |
| 4-Methyl umbelliferone | 4-methylumbelliferone | 330 | 450 |

-continued

| Compound R₂H | Structural formula | Excitation wavelength (ex.; nm) | Measurement wavelength (em.; nm) |
|---|---|---|---|
| Resorufin | (structure) | 540 | 580 |

This optical means can be utilized in the visible region, the ultraviolet region, the flourescent region, etc. depending upon the selection of the compound expressed by $R_2H$.

The following examples illustrate the present invention in greater detail.

PREPARTION EXAMPLE 1

Preparation of amoebocyte lysate:

About 100 ml of a hemolymphatic fluid was extracted from Tachypleus tridentatus (body weight about 2 kg), a Japanese horseshoe crab, in accordance with the method disclosed in Japanese Patent Publication No. 40131/76 while strictly avoiding contamination. Amoebocytes were separated by centrifugal separation, and washed with a 3% aqueous solution of sodium chloride to obtain amoebocyte pellets. to the amoebocyte pellets was added distilled water or buffer (tris-HCl, 0.05 M; $CaCl_2$, 0.001 M; NaCl 0.15 M; pH 7.2) in an amount one-tenth the volume of the starting hemolymphatic fluid. The mixture was well stirred by a sterilized homogenizer, frozen and melted, and then centrifuged for 15 minutes at a speed of 5000 rpm to form amoebocyte lysate Tachypleus (ALT for short).

PREPARATION EXAMPLE 2

The hemolymphatic fluid of Limulus polyphemus, a horseshoe crab occuring in U.S.A., was treated in the same way as in Preparation Example 1 to afford amoebocyte lysate Limulus (ALL for short). The ALL was gel-filtered using Sephadex G 50 by the method of N. S. Young, J. Clin. Invest., 51 1790 (1972) to form a fraction I containing an amidase precursor (ALL-FI for short).

EXAMPLE 1

An endotoxin of Salmonella minesota R 595 prepared by the method of H. Niwa et al., Japan J. Med. Sci. Biol. 26, 20 (1973) was caused to act on ALT and ALL of horseshoe crabs obtained in Preparation Examples 1 and 2, and the activity of resulting amidase was measured by using various syntehtic substrates. The results are shown in Table I. The method of measuring the activity of amidase on ALT and ALL was as follows:

A mixture consisting of 0.8 ml of 0.1 mM synthetic substrate dissolved in 0.1 M Tris-HCl buffer (pH 8.0), 50 μl of 0.5 M $MgCl_2$, and 20 μl of a 0.1% endotoxin solution was pre-incubated at 37° C. for 3 minutes. Then, 5 to 20 μl of the lysate was added and well mixed. The mixture was incubated at 37° C. for 15 minutes. After incubation, 100 μl of glacial actic acid was added to terminate the reaction. The absorbance of the resulting p-nitroaniline at 405 nm was measured.

Table 1 shows the amount in n moles of the p-nitroaniline calculated from the absorbance, and its relative amount in percent with the amount of p-nitroaniline determined with regard to the Bz-Ile-Glu(-γ-OMe)-Gly-Arg-PNA substrate being taken as 100.

Table 1

| | | ALT | | ALL | |
|---|---|---|---|---|---|
| No. | Substrate | Amount (n moles) | Relative activity (%) | Amount (n moles) | Relative activity (%) |
| 1 | Bz-Ile-Glu(-γ-OMe)-Gly-Arg-PNA | 17.7 | 100 | 4.4 | 100 |
| 2 | Tos-Ile-Glu-Gly-Arg-PNA | 7.3 | 41 | 14.1 | 318 |
| 3 | Boc-Val-Leu-Gly-Arg-PNA | 11.0 | 62 | 19.1 | 431 |
| 4 | Bz-Val-Gly-Arg-PNA | 12.4 | 70 | 10.1 | 227 |
| 5 | Bz-Phe-Val-Arg-PNA | 0.5 | 3 | 0.2 | 5 |
| 6 | Z-Gly-Pro-Arg-PNA | 0.5 | 3 | 0.4 | 9 |
| 7 | H.D.Phe-Pip-Arg-PNA | — | — | 0.3 | 6 |
| 8 | H.Glu-Gly-Arg-PNA | <0.1 | <1 | <0.1 | <3 |
| 9 | H.D Val-Leu-Arg-PNA | <0.1 | <1 | <0.1 | <3 |
| 10 | H.D. Val-Leu-Lys-PNA | <0.1 | <1 | <0.1 | <3 |
| 11 | H.D. Pro-Phe-Arg-PNA | <0.1 | <1 | <0.1 | <3 |

The synthetic substrates 1 and 2 shown in Table 1 are specific for blood coagulation factor Xa, and are very interesting in view of the fact that they are specific also for amidase resulting from the activation of an amoebocyte lysate of horseshoe crab by an endotoxin. The synthetic substrate 3 is a substrate synthesized by reference to the amino acid arrangement . . . Asp-Glu-Pro-Gly-Val-Leu-Gly-Arg- . . . (A-Chain) at the cleavage site of coagulogen caused by a clotting enzyme. The synthetic substrate 4 is a substrate for urokinase. The substrates 5, 6 and 7 are substrates for α-thrombin and do not have the essential amino acid structure in accordance with the present invention. The synthetic substrate 8 does not meet the requirement of the $R_1$ moiety of the component (A) used in this invention. The synthetic substrates 9 and 11 are for kallikrein, and the synthetic substrate 10 is for plasmin. These substrates 9 to 11 do not undergo the actions of enzymes in a blood coagulation-fibrinolysis system, and therefore, can permit the detection and determination of an endotoxin by a gellation phenomenon utilizing an amoebocyte lysate of horseshoe crab without the defect of the prior methods (the presence of various enzyme systems present in the blood causes the non-specific gellation of the amoebocyte lysate, which in turn leads to the failute of detecting and determining the endotoxin), and the determination of an endotoxin in protease preparations.

EXAMPLE 2

Using ALT, the endotoxin of Salmonella minesota R595, and Bz-Ile-Glu-Gly-Arg-PNA, the correlation between the concentration of the endotoxin and the absorbance of the resulting PNA was examined. Table 2 and FIG. 1 show the absorbance of PNA at a substrate concentration of 0.05 mM after the reaction mixture was incubated for 15, 30, and 60 minutes.

Table 2

| Concentration of endotoxin | Absorbance of PNA after an incubation time of | | |
|---|---|---|---|
| ($\mu$g/ml) | 15 minutes | 30 minutes | 60 minutes |
| 1 | 0.38 | 0.38 | 0.38 |
| $10^{-1}$ | 0.34 | 0.37 | 0.38 |
| $10^{-2}$ | 0.23 | 0.34 | 0.37 |
| $10^{-3}$ | 0.07 | 0.25 | 0.35 |
| $10^{-4}$ | 0.01 | 0.13 | 0.30 |
| $10^{-5}$ | 0.00 | 0.05 | 0.18 |
| $10^{-6}$ | | 0.01 | 0.08 |
| $10^{-7}$ | | 0.00 | 0.03 |
| $10^{-8}$ | | | 0.01 |

As is seen from Table 2 and FIG. 1, the absorbance of PNA increases with increasing concentration of the endotoxin, and the correlation between the concentration of the endotoxin and the absorbance of PNA is straightly linear within an endotoxin concentration range of $2 \times 10^{-7}$ to $2 \times 10^{-4}$ $\mu$g/ml. This shows that the method of this invention has high sensitivity and stability as compared with the detection limit of the conventional endotoxin determining method which is $10^{-3}$ to $10^{-4}$ $\mu$g/ml.

EXAMPLE 3

Using ALL-FI, and Z-Ile-Glu-Gly-Arg-PNA, endotoxins derived from various species of bacteria were determined. The ranges of the concentrations of the endotoxins that could be detected were determined from the correlation chart of the concentrations of various endotoxins versus the absorbance of PNA which was prepared in accordance with Example 2. The results are shown in Table 3.

Table 3

| Endotoxins | Endotoxin concentrations ($\mu$g/ml) detected |
|---|---|
| Endotoxin derived from | |
| Salmonella minesota R595 | $2 \times 10^{-5}$ to $2 \times 10^{-7}$ ($5 \times 10^{-4}$) |
| E. coli UKTB | $6 \times 10^{-5}$ to $6 \times 10^{-7}$ ($2 \times 10^{-4}$) |
| Shigella K$_3$ | $2 \times 10^{-4}$ to $2 \times 10^{-6}$ ($4 \times 10^{-3}$) |
| E. coli 0111:B$_4$ | $5 \times 10^{-4}$ to $5 \times 10^{-6}$ ($3 \times 10^{-3}$) |
| Ps. aeruginosa | $2 \times 10^{-3}$ to $2 \times 10^{-5}$ ($5 \times 10^{-1}$) |

Note:
The figures in the parentheses are the concentrations of the endotoxins which were determined by the conventional gellation method.

It can be seen from Table 3 that the method of this invention can detect and determine bacterial endotoxins with a sensitivity 100 to 1000 times as high as that of the conventional gallation method using ALL, and permits the detection of endotoxins using an amoebocyte lysate of horseshoe crab.

EXAMPLE 4

A specific peptide fluorogenic substrate D-Val-L-Leu-Gly-L-Arg-Resorufin ester ($[\alpha]_D^{20} = -13.8$ C=0.46 in 80% DMSO) was first dissolved in dimethylsulfoxide (DMSO, analytical reagent), and the solution was diluted to give a final concentration of 0.1 mM using 50 mM Tris-HCl Buffer (pH 8.0) containing 100 mM NaCl and 10 mM CaCl$_2$.

Using a fluoroescence spectrophotometer (for example, Hitachi, model MPF-2A), 2.5 ml of the 0.1 mM substrate buffer solution was added to a cuvette and preincubated at 37° C. for 2.5 minutes.

10 $\mu$l of ALL-FI (OD$^{280}$=0.3/ml) activated with endotoxin (E. Coli 0111:B$_4$) was added, and mixed immediately. The recorder for measurement of excitation at 540 nm and emission at 580 nm was started.

Figure 2:
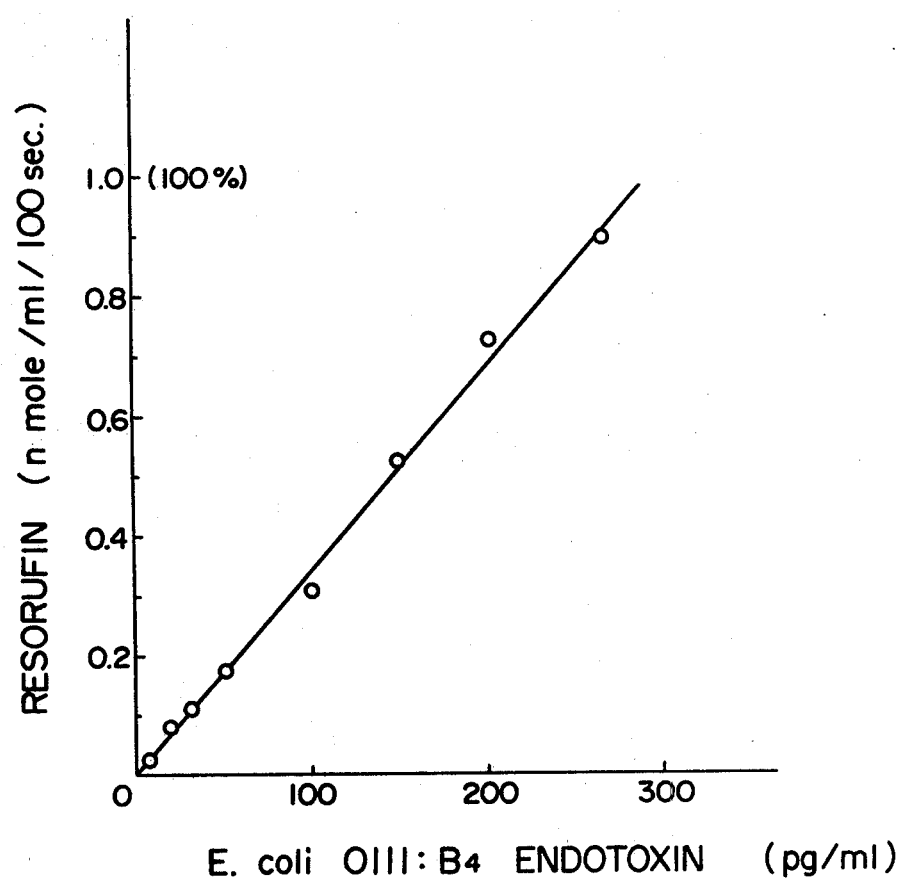

The increase of the relative fluorescence (%) was read at regular time intervals after a lapse of 100 seconds. The assay was performed according to the varying amounts of the endotoxin. The instrument was standardized so that a 10 $\mu$M solution of Resorufin in 0.1% DMSO would give 1.0 relative fluorescence unit. The results are shown in FIG. 2.

What we claim is:

1. A process for determining a bacterial endotoxin, which comprises contacting an assay sample with (A) a material selected from the group consisting of an amoebocyte lysate of horseshoe crab and a pro-clotting enzyme separated from the lysate, and (B) a peptide-type substrate of the formula $$R_1—Gly—Arg—R_2$$

wherein R$_1$ represents a member selected from the group consisting of an L-amino acid moiety whose N-terminal is protected by a protective group, a peptide moiety consisting of an L-amino acid and protected by a protective group at its N-terminal, a D-amino acid substituted L-amino acid moiety, and a D-amino acid substituted peptide moiety consisting of an L-amino acid, and is bonded to the amino group of the glycine moiety expressed by Gly through a peptide bond; and R$_2$ represents a chromogenic moiety which is bonded to the C-terminal of an L-arginine moiety expressed by Arg through an acid amide bond and/or ester bond and can be enzymatically hydrolyzed in the presence of the material (A) and the endotoxin to liberate R$_2$H, and/or its mineral acid salt, and detecting the resulting R$_2$H in which R$_2$ is as defined above.

2. The process of claim 1 wherein the protective group is a member selected from the group consisting of an $\alpha$-N-benzoyl group, and $\alpha$-N-carbobenzoxy group, and N-tert.-butoxycarbonyl group and a p-toluenesulfonyl group.

3. The process of claim 1 wherein R$_2$ is a member selected from the group consisting of para-nitroanilide, 5-nitro-$\alpha$-naphthylamide, $\alpha$-naphthylamide, $\alpha$-naphthyl ester, $\beta$-naphthyl, ester indoxyl ester, N-methyl indoxyl ester, (4-methyl)umbelliferyl ester and resorufin ester.

4. A reagent for the detection or determination of an endotoxin, comprising
   (A) a material selected from the group consisting of an amoebocyte lysate of horseshoe crab and a pro-clotting enzyme separated from the lysate, and
   (B) a peptide-type substrate of the formula $$R_1—Gly—Arg—R_2$$

wherein R$_1$ represents a member selected from the group consisting of an L-amino acid moiety whose N-terminal is protected by a protective group, a peptide moiety consisting of an L-amino acid and protected by a protective group at its N-terminal, a D-amino acid substituted L-amino acid moiety, and a D-amino acid substituted peptide moiety consisting of an L-amino acid, and is bonded to the amino group of the glycine moiety expressed by Gly through a peptide bond; and $R_2$ represents a chromogenic moiety which is bonded to the C-terminal of an L-arginine moiety expressed by Arg through an acid amide bond and/or ester bond and can be enzymatically hydrolyzed in the presence of the material (A) and the endotoxin to liberate $R_2H$ for detection or determination of the endotoxin.

5. The reagent of claim 4 wherein the protective group is a member selected from the group consisting of an α-N-benzoyl group, and α-N-carbobenzoxy group, and N-tert.-butoxycarbonyl group and a p-toluenesulfonyl group.

6. The reagent of claim 4 wherein $R_2$ is a member selected from the group consisting of para-nitroanilide, 5-nitro-α-naphthylamide, α-naphthylamide, α-naphthyl ester, β-naphthyl ester, indoxyl ester, N-methyl indoxyl ester, (4-methyl) umbelliferyl ester and resorufin ester.

* * * * *